(12) United States Patent
Zhao et al.

(10) Patent No.: US 9,700,307 B2
(45) Date of Patent: Jul. 11, 2017

(54) SUTURING NAIL

(71) Applicant: SHENZHEN INSTITUTES OF ADVANCED TECHNOLOGY CHINESE ACADEMY OF SCIENCES, Guangdong (CN)

(72) Inventors: Guoru Zhao, Guangdong (CN); Yongfeng Wang, Guangdong (CN)

(73) Assignee: Shenzhen Institutes of Advanced Technology Chinese Academy of Sciences, Guangdong (CN)

(*) Notice: Subject to any disclaimer, the term of this patent is extended or adjusted under 35 U.S.C. 154(b) by 0 days.

(21) Appl. No.: 14/372,500

(22) PCT Filed: Feb. 13, 2014

(86) PCT No.: PCT/CN2014/072016
§ 371 (c)(1),
(2) Date: Jul. 16, 2014

(87) PCT Pub. No.: WO2014/194692
PCT Pub. Date: Dec. 11, 2014

(65) Prior Publication Data
US 2016/0270782 A1  Sep. 22, 2016

(30) Foreign Application Priority Data
Jun. 5, 2013 (CN) .......................... 2013 1 0221117

(51) Int. Cl.
A61B 17/08 (2006.01)
A61B 17/064 (2006.01)
A61B 17/00 (2006.01)

(52) U.S. Cl.
CPC  A61B 17/0644 (2013.01); A61B 2017/00946 (2013.01); A61B 2017/0641 (2013.01)

(58) Field of Classification Search
CPC .............. A61B 17/0487; A61B 17/064; A61B 17/0642; A61B 17/0643; A61B 17/0644;
(Continued)

(56) References Cited

U.S. PATENT DOCUMENTS

| | | | |
|---|---|---|---|
| 5,372,604 A | 12/1994 | Trott | |
| 7,060,021 B1* | 6/2006 | Wilk | ................ A61B 17/00234 128/898 |
| 2010/0198254 A1* | 8/2010 | Schaeffer | ........... A61B 17/0057 606/213 |

OTHER PUBLICATIONS

Communication From the Chinese Patent Office Regarding a Counterpart Foreign Application Dated Oct. 20, 2014.

* cited by examiner

Primary Examiner — David C Eastwood
Assistant Examiner — Kankindi Rwego
(74) Attorney, Agent, or Firm — Rosenberg, Klein & Lee

(57) ABSTRACT

A suturing nail includes a first nail body a second nail body being intertwined mutually to form a helix portion; a first nail crown extending from an end of the first nail body; a second nail crown extending from an end of the second nail body and opposite to the first nail crown, the first and the second nail crown being located on the same side of the helix portion and perpendicular to the helix portion; a first nail leg extending from the other end of the first nail body; a second nail leg extending from the other end of the second nail body and being spaced from the first nail, the first and the second nail leg are located on the same side of the helix portion, the first nail leg and the second nail leg are parallel to the helix portion. The suturing nail is not deformed easily.

5 Claims, 4 Drawing Sheets

(58) Field of Classification Search
CPC ..... A61B 17/08; A61B 17/083; A61B 17/085; A61B 17/68; A61B 17/7019; A61B 17/7028; A61B 17/122; A61B 17/1222; A61B 17/127; A61B 17/128; A61B 17/1285; A61B 2017/0488; A61B 2017/049; A61B 2017/0641; A61B 2017/0645; A61B 2017/0646; A61B 2017/0647; A61B 2017/0648; A61B 2017/081; A61B 2017/086; A61B 2017/088; A61B 2017/1225; F16B 15/00; F16B 15/0007; F16B 15/0015; F16B 15/0092; F16B 15/02; F16B 15/04; F16B 15/06; F16B 15/08

See application file for complete search history.

US 9,700,307 B2

SUTURING NAIL

FIELD OF THE INVENTION

The present disclosure relates to a medical surgery suture instrument, more particularly relates to a suturing nail.

BACKGROUND OF THE INVENTION

Working principle of a medical surgery suture instrument is substantially the same as that of a stapler. The operating process is: the suturing nail is received in a nail box, and a tissue to be sutured is placed between the suturing nail and an anvil. A distance between the anvil and the suturing nail is adjusted, then the suturing nail penetrates the tissue and then is bended in the anvil, thereby suturing the tissue. The employment of the suturing nail reduces a surgical operation time and greatly enhances an operation efficiency thereof, and in addition, a success ratio of the surgery is highly improved.

However, a conventional suturing nail employed in the surgery general has defects as follow: when the conventional suturing nail is used to suture a relative thicker and larger tissue, due to a shortcoming of an intensity and toughness of the conventional suturing nail, the suturing nail may be not retained in an original suturing state and be deformed easily.

SUMMARY OF THE INVENTION

According to this, it is necessary to provide a suturing nail which is not deformed easily during the suturing.

A suturing nail includes a first nail body; a second nail body, the first nail body and the second nail body being intertwined mutually to form a helix portion; a first nail crown extending from an end of the first nail body; a second nail crown extending from an end of the second nail body and opposite to the first nail crown, the first nail crown and the second nail crown being located on the same side of the helix portion and perpendicular to an axis of the helix portion; a first nail leg extending from the other end of the first nail body; and a second nail leg extending from the other end of the second nail body, where the first nail leg and the second nail leg are located on the same side of the helix portion, the first nail leg is spaced from the second nail leg, the first nail leg and the second nail leg are parallel to the axis of the helix portion.

When the suturing nail is in use, both the first nail leg and the second nail leg penetrate the tissue be sutured under an external force, then the first nail leg is bended towards the side of the second nail crown, and the second nail leg is bended towards the side of the first nail crown, thus both the first nail leg and the second nail leg penetrate the tissue to be sutured again, and the suturing nail forms a structure similar to B-shape, a suture is completed. The middle portion of the structure similar to B-shape of the suturing nail is consisted of the helix portion which is formed by intertwining of the first nail body and the second nail body, thus the suturing nail has much higher intensity and toughness, which is not deformed easily.

BRIEF DESCRIPTION OF THE DRAWINGS

The detailed description is described with reference to the accompanying figures. These and other objects, features, and advantages of the present invention will become readily apparent. The use of the same reference numbers in the description and the figures indicate similar or identical items. The drawings are not necessarily to scale, the emphasis instead generally being placed upon illustrating the principles of the invention.

DETAILED DESCRIPTION OF THE EMBODIMENTS

Embodiments of the suturing nail are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. As used herein, the term "and/or" includes any and all combinations of one or more of the associated listed items.

Figure 1:
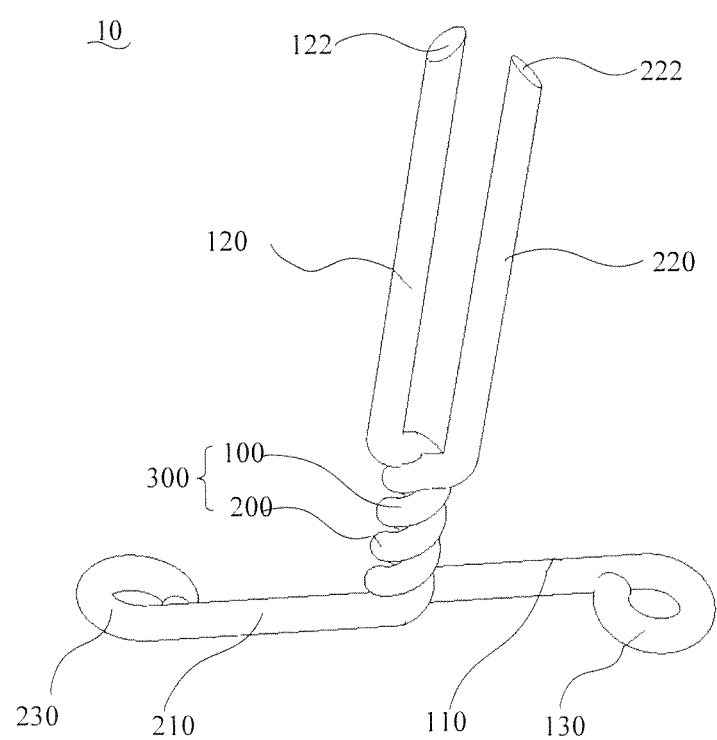
FIG. 1 is an isometric, schematic view of a suturing nail of an embodiment.

Referring to FIG. 1, an embodiment of a suturing nail 10 includes a first nail body 100 and a second nail body 200. The first nail body 100 and the second nail body 200 are intertwined mutually to form a helix portion 300.

In the illustrated embodiment, the first nail body 100 and the second nail body 200 are made of same material and have same structures. In the illustrated embodiment, a cross-sectional view of the first nail body 100 and a cross-sectional view of the second nail body 200 are circular, the first nail body 100 and the second nail body 200 are made of titanium.

A first nail crown 110 extends from an end of the first nail body 100, a second nail crown 210 extends from an end of the second nail body 200 and opposite to the first nail crown 110. The first nail crown 110 and the second nail crown 210 are located on the same side (end) of the helix portion 300 and perpendicular to the helix portion 300, i.e. the first nail crown 110 and the second nail crown 210 are parallel to each other, the helix portion 300 is perpendicular to the plane where the first nail crown 110 and the second nail crown 210 are located.

A first nail leg 120 extends from the other end of the first nail body 100; a second nail leg 220 extends from the other end of the second nail body 200. The first nail leg 120 and the second nail leg 220 are located on the same side (end) of the helix portion 300. The first nail leg 120 is spaced from the second nail leg 220, and the first nail leg 120 and the second nail leg 220 are parallel to an axis of the helix portion 300. In the illustrated embodiment, a first end face 122 of the first nail leg 120 and a second end face 222 of the second nail leg 220 are inclined surfaces. The first nail leg 120 and the second nail leg 220 with the inclined surfaces can easily penetrate the tissue to be sutured.

In the illustrated embodiment, a length of the first nail leg 120 is equal to a length of the second nail leg 220.

When the suturing nail 10 is in use, under an external force, the first nail leg 120 is bended towards the second nail crown 210, and the second nail leg 220 is bended towards of the first nail crown 110, such that a standard B-shape structure is formed (referring to FIG. 2), the tissue to be sutured bears a much more uniform force. Alternatively, in the other embodiments, a length of the first nail leg 120 differs from a length of the second nail leg 220. When the suturing nail 10 is in use, the suturing nail 100 forms a structure similar to B-shape, which can meet some special suturing requirements.

In the illustrated embodiment, a distance between the first nail leg 120 and the second nail leg 220 varies in a range of 1 to 2 times of a diameter of the first nail body 100. If too narrow, the first nail leg 120 and the second nail leg 220 may penetrate the same position of the tissue; if too broad, the space generated within the structure similar to B-shape is relatively small, which does not facilitate the suturing of a thicker tissue.

When the suturing nail 10 is in use, under an external force, both the first nail leg 120 and the second nail leg 220 penetrate the tissue to be sutured, then under an external force, the first nail leg 120 is bended towards the second nail crown 210, and the second nail leg 220 is bended towards the first nail crown 110, thus both the first nail leg 120 and the second nail leg 220 penetrate the tissue to be sutured again, and the suturing nail 10 forms the structure similar to B-shape. The suturing nail 10 penetrates the tissue for two times during the suturing, thus the tissue can be more tightly sutured by the suturing nail 10. Moreover, the middle portion of the structure similar to B-shape of the suturing nail 10 is consisted of the helix portion 300 which is formed by intertwining of the first nail body 100 and the second nail body 200, thus the suturing nail 10 has much higher intensity and toughness comparing with the conventional suturing nail. Whereby, the middle portion of the structure similar to B-shape of the conventional suturing nail is formed by two bended free ends, which is similar to the common staple, the two bended free ends are deformed easily. When the suturing nail 10 is used to suture a thicker tissue, the original suturing state can be maintained for a long time, the suturing nail 10 is not deformed easily. Furthermore, the suturing nail 10 has an excellent performance in molding, and is easy to operate, and have a relative higher suturing efficiency.

In an embodiment, a hollow first ring 130 is bended from a distal end of the first nail crown 110, a hollow second ring 230 is bended from a distal end of the second nail crown 210. The first ring 130, the second ring 230, the first nail crown 110, and the second nail crown 210 are arranged in the same plane. When the suturing nail 10 is in use, the first nail leg 120 is bended into the second ring 230, and the second nail leg 220 is bended into the first ring 130, the suturing nail 10 forms the structure similar to B-shape.

Figure 2:
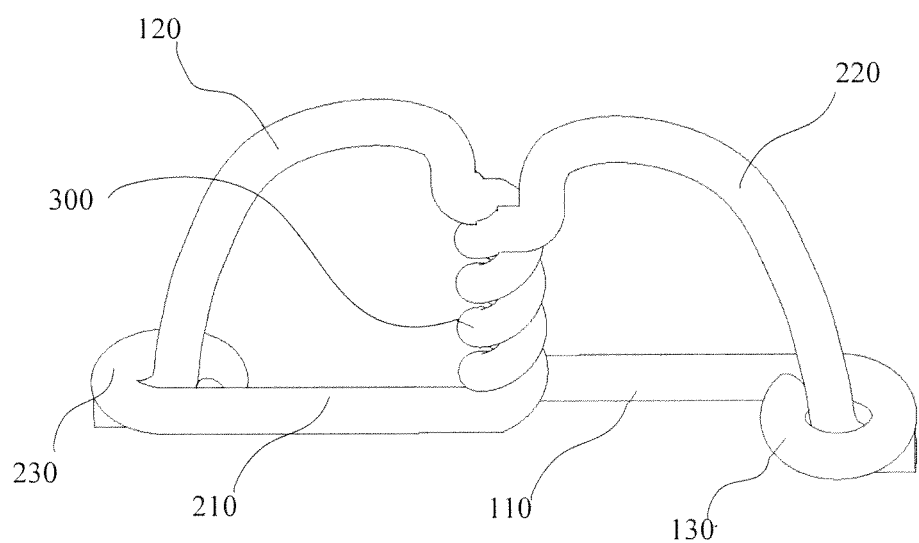
FIG. 2 is an operating state diagram of the suturing nail shown in FIG. 1.

Referring to FIG. 2, when the suturing nail 10 is in use, under an external force, both the first nail leg 120 and the second nail leg 220 penetrate the tissue to be sutured, then under an external force, the first nail leg 120 is bended into the second ring 230, and the second nail leg 220 is bended into the first ring 130, thus both the first nail leg 120 and the second nail leg 220 penetrate the tissue to be sutured again. After the first nail leg 120 is inserted into the second ring 230 and the second nail leg 220 is inserted into the first ring 130, under an external force, a distal end of the first nail leg 120 is bended and then latched with the first ring 130, a distal end of the second nail leg 220 is bended and then latched with the second ring 230, thus the suturing is accomplished. The tissue can be more tightly sutured by the suturing nail 10, thus avoiding an infection and other complication diseases, the original suturing state of the suturing nail 10 can be maintained for a long time, and a great applicability is obtained.

In the illustrated embodiment, the first ring 130 and the second ring 230 are central symmetrical to each other relative to the helix portion 300, i.e. the second ring 230 can be approximately coincided with the first ring 130 after the second ring 230 is rotated about the helix portion 300 for 180 degrees.

Figure 3:
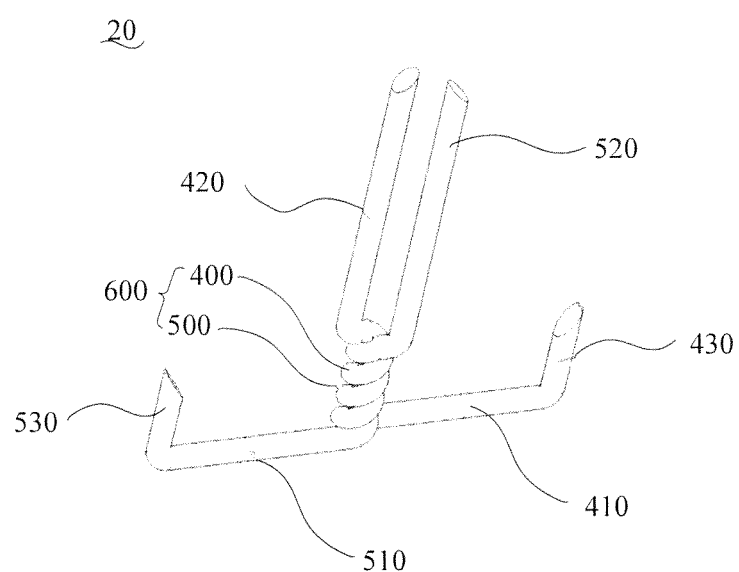
FIG. 3 is an isometric, schematic view of a suturing nail of another embodiment.
Figure 4:
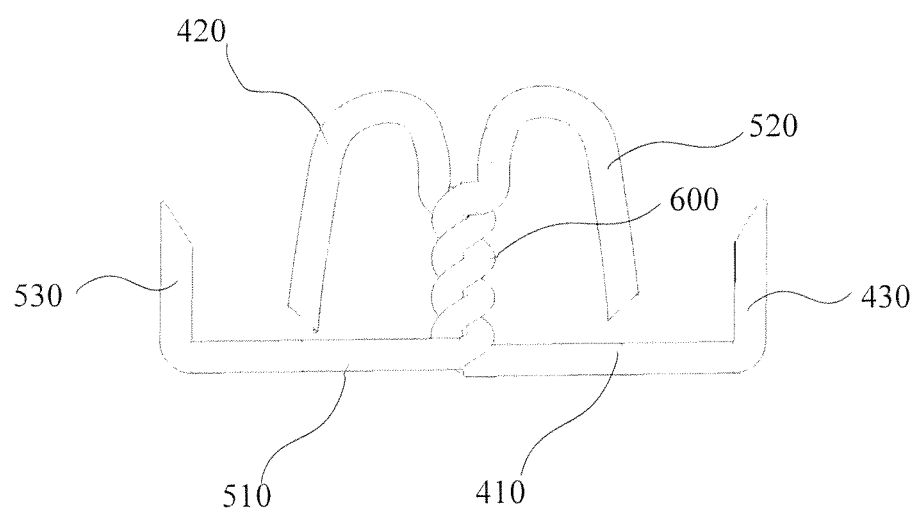
FIG. 4 is an operating state diagram of the suturing nail shown in FIG. 3.

Referring to FIG. 3 and FIG. 4, alternatively, an embodiment of a suturing nail 20 includes a first nail body 400 and a second nail body 500. The first nail body 400 and the second nail body 500 are intertwined mutually to form a helix portion 600.

A first nail crown 410 extends from an end of the first nail body 400, a second nail crown 510 extends from an end of the second nail body 500 and opposite to the first nail crown 410, the first nail crown 410 and the second nail crown 510 are located on the same side (end) of the helix portion 600 and perpendicular to the helix portion 600. A first nail leg 420 extends from the other end of the first nail body 400; a second nail leg 520 extends from the other end of the second nail body 500. The first nail leg 420 and the second nail leg 520 are located on the same side (end) of the helix portion 600, the first nail leg 420 is spaced from the second nail leg 520; the first nail leg 420 and the second nail leg 520 are parallel to the helix portion 600.

A third nail leg 430 curvedly extends from a distal end of the first nail crown 410, the third nail leg 430 is perpendicular to the first nail crown 410. A fourth nail leg 530 curvedly extends from a distal end of the second nail crown 510, the fourth nail leg 530 is perpendicular to the second nail crown 510. The third nail leg 430, the fourth nail leg 530, the first nail leg 420, and the second nail leg 520 extends along a same direction, i.e. the third nail leg 430 and the fourth nail leg 530 are parallel to the helix portion 600. In an embodiment, a length ratio of the third nail leg 430 to the first nail leg 420 is in a range of 1:3 to 1:4, a length ratio of the fourth nail leg 530 to the second nail leg 520 is in a range of is 1:3 to 1:4. In an embodiment, a length ratio of the third nail leg to the helix portion is in a range of 3:1 to 5:1, a length ratio of the fourth nail leg to the helix portion is in a range of is 3:1 to 5:1.

An end face of a free end of the third nail leg 430 and an end face of a free end of the fourth nail leg 530 are inclined surfaces.

When the first nail leg 420 is bended towards the second nail crown 510, and the second nail leg 520 is bended towards the first nail crown 410, the suturing nail 20 forms a structure similar to B-shape. In the structure similar to B-shape, a distance between the third nail leg 430 and the fourth nail leg 530 is greater than that between a distal end of the first nail leg 420 and a distal end of the second nail leg 520, i.e. the distal end of the first nail leg 420 and the fourth nail leg 530 form the upper end (lower end) of the structure similar to B-shape, the helix portion 600 forms the middle portion of the structure similar to B-shape, the distal end of the second nail leg 520 and the third nail leg 430 form the lower end (upper end) of the structure similar to B-shape, and the third nail leg 430 and the fourth nail leg 530 are located on the outer of the B-shape structure.

When the suturing nail 20 is in use, under an external force, the first nail leg 420, the second nail leg 520, the third nail leg 430, and the fourth leg 530 penetrate the tissue to be sutured. Moreover, under an external force, the first nail leg 420 is bended towards the side of the second nail crown 510, and the second nail leg 520 is bended towards the side of the first nail crown 410, thus both the first nail leg 420 and the second nail leg 520 penetrate the tissue to be sutured again, and the suturing nail 20 forms the structure similar to the B-shape, thus the suturing is accomplished. The tissue can be more tightly sutured by the suturing nail 20, thus avoiding an infection and other complication diseases, the original suturing state of the suturing nail 10 can be maintained for a long time, and a great applicability is obtained.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. A suturing nail, comprising:
   a first nail body;
   a second nail body, the first nail body and the second nail body being intertwined mutually to form a longitudinally extended helix portion;
   a first nail crown extending from an end of the first nail body;
   a second nail crown extending from an end of the second nail body in a direction opposite to the first nail crown, the first nail crown and the second nail crown being located on the same side of the helix portion and extend perpendicular to a longitudinal axis of the helix portion;
   a first nail leg formed at another end of the first nail body and extending from the helix portion; and
   a second nail leg formed at another end of the second nail body and extending from the helix portion, wherein the first nail leg and the second nail leg are located on the same side of the helix portion, the first nail leg is spaced from the second nail leg, the first nail leg and the second nail leg are each disposed parallel to the longitudinal axis of the helix portion;
   a third nail leg curvedly extending from a distal end of the first nail crown in a direction toward the helix portion, the third nail leg being perpendicular to the first nail crown, a fourth nail leg curvedly extending from a distal end of the second nail crown in a direction toward the helix portion, the fourth nail leg being perpendicular to the second nail crown; the third nail leg and the fourth nail leg are each disposed parallel to the longitudinal axis of the helix portion;
   the first nail leg being configured to penetrate tissue then subsequently being bent toward the second nail crown to again penetrate tissue, and the second nail leg being configured to penetrate tissue then subsequently being bent toward the first nail crown to again penetrate tissue, and thereby forms a suture; and
   wherein a length ratio of the third nail leg to the first nail leg is in a range of 1:3 to 1:4, a length ratio of the fourth nail leg to the second nail leg is in a range of 1:3 to 1:4.

2. The suturing nail according to claim 1, wherein an end face of a free end of the third nail leg and an end face of a free end of the fourth nail leg are inclined surfaces.

3. The suturing nail according to claim 1, wherein an end face of a free end of the first nail leg and an end face of a free end of the second nail leg are inclined surfaces.

4. The suturing nail according to claim 1, wherein both the first nail body and the second nail body are cylindrical titanium needles.

5. The suturing nail according to claim 4, wherein a distance between the first nail leg and the second nail leg is 1 to 2 times of a diameter of the first nail body.

* * * * *